US00PP31264P2

(12) United States Plant Patent

Eveleens et al.

(10) Patent No.: US PP31,264 P2

(45) Date of Patent: Dec. 24, 2019

(54) *HYDRANGEA* PLANT NAMED 'HOKOMARORE'

(50) Latin Name: *Hydrangea macrophylla*
Varietal Denomination: Hokomarore

(71) Applicants: KOLSTER HOLDING B.V., Boskoop (NL); HORTEVE BREEDING B.V., Aalsmeer (NL)

(72) Inventors: Cornelis P. Eveleens, Aalsmeer (NL); Peter R. Kolster, Boskoop (NL)

(73) Assignees: Kolster Holding B.V., Baskoop (NL); Horteve Breeding B.V., Aalsmeer (NL)

( * ) Notice: Subject to any disclaimer, the term of this patent is extended or adjusted under 35 U.S.C. 154(b) by 0 days.

(21) Appl. No.: 15/999,929

(22) Filed: Aug. 31, 2018

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
See application file for complete search history.

(56) References Cited

PUBLICATIONS

UPOV hit on a *Hydrangea* plant named, 'Hokomarore', QZ PBR 20180535, published Apr. 16, 2018.*

* cited by examiner

*Primary Examiner* — Anne Marie Grunberg
(74) *Attorney, Agent, or Firm* — C. A. Whealy

(57) ABSTRACT

A new and distinct cultivar of *Hydrangea* plant named 'Hokomarore', characterized by its upright and spreading plant habit; moderately vigorous to vigorous growth habit and moderate to rapid growth rate; freely branching habit with strong and thick sturdy stems; large mophead-type inflorescences with red purple-colored sterile flowers; and good postproduction longevity.

2 Drawing Sheets

Botanical designation: *Hydrangea macrophylla.*
Cultivar denomination: 'HOKOMARORE'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hokomarore'.

The new *Hydrangea* is a naturally-occurring branch mutation of *Hydrangea macrophylla* 'Hokomarevo', disclosed in U.S. Plant Pat. No. 22,260. The new *Hydrangea* plant was discovered and selected by the Inventors on a single flowering plant from within a population of plants of 'Hokomarevo' in a controlled greenhouse environment in Boskoop, The Netherlands in 2016.

Asexual reproduction of the new *Hydrangea* plant by vegetative terminal cuttings in a controlled environment in Boskoop, The Netherlands since 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hokomarore'. These characteristics in combination distinguish 'Hokomarore' as a new and distinct *Hydrangea* plant:

1. Upright and spreading plant habit.
2. Moderately vigorous to vigorous growth habit and moderate to rapid growth rate.
3. Freely branching habit with strong and thick sturdy stems.
4. Large mophead-type inflorescences with red purple-colored sterile flowers.
5. Good postproduction longevity.

Plants of the new *Hydrangea* can be compared to plants of the mutation parent, 'Hokomarevo'. Plants of the new *Hydrangea* differ primarily from plants of 'Hokomarevo' in sterile flower color as sterile flower sepals of plants of the new *Hydrangea* are darker red purple in color than sterile flower sepals of plants of 'Hokomarevo'. In addition, sterile flower sepals of plants of the new *Hydrangea* maintain their red purple color with development whereas sterile flower sepals of plants of 'Hokomarevo' become red purple and green with development.

Plants of the new *Hydrangea* can be compared to plants of the *Hydrangea macrophylla* 'Magical Opal', disclosed in U.S. Plant Pat. No. 20,483. In side-by-side comparisons plants of the new *Hydrangea* differ primarily from plants of 'Magical Opal' in the following characteristics:

1. Plants of the new *Hydrangea* have shorter lateral branches than plants of 'Magical Opal'.
2. Plants of the new *Hydrangea* have smaller leaves than plants of 'Magical Opal'.

3. Plants of the new *Hydrangea* have smaller inflorescences with smaller sterile flower sepals than plants of 'Magical Opal'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'Hokomarore' grown in a container.

The photograph on the second sheet is a close-up view of a typical inflorescence of 'Hokomarore'.

DETAILED BOTANICAL DESCRIPTION

Plants used in the aforementioned photographs and in the following description were grown during the summer in 19-cm containers in a glass-covered greenhouse in Boskoop, The Netherlands and under cultural practices typical of commercial *Hydrangea* production. During the production of the plants, day temperatures ranged from 16° C. to 30° C. and night temperatures ranged from 10° C. to 18° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hokomarore'.

Parentage: Naturally-occurring branch mutation of *Hydrangea macrophylla* 'Hokomarevo', disclosed in U.S. Plant Pat. No. 22,260.

Propagation:

- *Type cutting*.—By vegetative terminal cuttings.
- *Time to initiate roots, summer*.—About three weeks at temperatures about 15° C. to 25° C.
- *Time to produce a rooted young plant, summer*.—About six weeks at temperatures about 15° C. to 25° C.
- *Root description*.—Medium in thickness, fibrous; typically creamy white in color, actual color of the roots is dependent on substrate composition, water quality, fertilizer type and formulation, substrate temperature and physiological age of roots.
- *Rooting habit*.—Moderately freely branching; medium density.

Plant description:

- *Plant and growth habit*.—Upright and spreading plant habit; inverted triangle in shape; strong and sturdy lateral branches; moderate to rapid growth rate and moderately vigorous to vigorous growth habit.
- *Plant height*.—About 48.6 cm.
- *Plant diameter or area of spread*.—About 54.2 cm.

Lateral branch description:

- *Branching habit*.—Freely branching habit; when pinched, about nine lateral branches develop per plant.
- *Length*.—About 24.6 cm.
- *Diameter*.—About 5 mm.
- *Internode length*.—About 6.6 cm.
- *Texture*.—Smooth, glabrous; fully developed, woody.
- *Aspect*.—Upright to about 25° from vertical.
- *Strength*.—Strong, sturdy.
- *Color*.—When developing: Close to 144A. Developed: Close to 146B; at the internodes, tinged with close to N186B; when woody, close to N199C and N199D.
- *Lenticels*.—Density: Dense. Length: About 4 mm. Diameter: About 1 mm. Color: Close to between N186B and N186C.

Leaf description:

- *Arrangement*.—Opposite, simple.
- *Length*.—About 11.9 cm.
- *Width*.—About 9.2 cm.
- *Shape*.—Broadly ovate.
- *Apex*.—Apiculate.
- *Base*.—Short attenuate to truncate.
- *Margin*.—Serrate.
- *Texture, upper surface*.—Smooth to slightly rugose, glabrous.
- *Texture, lower surface*.—Smooth to moderately rugose, glabrous.
- *Venation pattern*.—Pinnate.
- *Color*.—Developing leaves, upper surface: Close to 143A. Developing leaves, lower surface: Close to 144A. Fully expanded leaves, upper surface: Close to between NN137A and 147A; venation, close to 144A. Fully expanded leaves, lower surface: Close to 147B; venation, close to 144B.
- *Petioles*.—Length: About 3.6 cm. Diameter: About 4 mm. Texture and luster, upper and lower surfaces: Smooth, glabrous; slightly glossy. Color, upper and lower surfaces: Close to 144A.

Flower description:

- *Flower type and habit*.—Showy sterile flowers and small inconspicuous fertile flowers arranged on mophead-type terminal panicles; panicles flattened globular in shape; fertile flowers face mostly upright and sterile flowers face upright to outwardly depending on their position in the inflorescence.
- *Fragrance*.—None detected.
- *Natural flowering season*.—Plants flower from late spring to late summer in The Netherlands.
- *Flower longevity*.—Fertile flowers last about two days on the plant, fertile flowers not persistent; sterile flowers last about six weeks on the plant, sterile flowers persistent.
- *Quantity of flowers*.—Freely flowering habit; about 55 fertile flowers per panicle and about 130 sterile flowers per panicle.
- *Panicle height*.—About 10.5 cm.
- *Panicle diameter*.—About 18.3 cm.
- *Fertile flower buds*.—Length: About 4 mm. Diameter: About 2.5 mm. Shape: Obovate. Color: Close to 63D; towards the base, close to 144D.
- *Sterile flower buds*.—Length: About 8 mm. Diameter: About 1.8 cm. Shape: Cup-shaped. Color: Close to 63D.
- *Fertile flower diameter*.—About 4 mm.
- *Fertile flower depth (height)*.—About 4 mm.
- *Sterile flower diameter*.—About 3.4 cm.
- *Sterile flower depth (height)*.—About 1.9 cm.
- *Petals, fertile flowers*.—Quantity and arrangement: Five in a single whorl. Length: About 4 mm. Width:

About 2.5 mm. Shape: Ovate, concave. Apex: Acute. Base: Cuneate. Margin: Entire. Texture and luster, upper and lower surfaces: Smooth, glabrous; matte. Color: When opening, upper surface: Close to 76B; towards the margins, close to 76D. When opening, lower surface: Close to 76D; towards the margins, close to 76B. Fully opened, upper surface: Close to 76A; towards the margins, close to 76C; color does not change with development. Fully opened, lower surface: Close to 76A; color does not change with development.

*Petals, sterile flowers*.—Quantity and arrangement: About four in a single whorl. Length: About 3.5 mm. Width: About 2 mm. Shape: Ovate, concave. Apex: Acute. Base: Cuneate. Margin: Entire. Texture and luster, upper and lower surfaces: Smooth, glabrous; matte. Color: When opening, upper surface: Close to 76B; towards the margins, close to 76D. When opening, lower surface: Close to 76D; towards the margins, close to 76B. Fully opened, upper surface: Close to 76A; towards the margins, close to 76C; color does not change with development. Fully opened, lower surface: Close to 76A; color does not change with development.

*Sepals, fertile flowers*.—Quantity and arrangement: About five in a single whorl. Length: About 2 mm. Width: About 1.5 mm. Shape: Ovate. Apex: Broadly acute. Base: Broadly cuneate. Margin: Entire. Texture and luster, upper surface: Smooth, glabrous; matte. Texture and luster, lower surface: Smooth, glabrous; slightly glossy. Color: When opening and fully opened, upper surface: Close to 70D; distally, close to 144B; color does not change with development. When opening and fully opened, lower surface: Close to 70C to 70D; towards the apex, close to 144A to 144B; color does not change with development.

*Sepals, sterile flowers*.—Quantity and arrangement: Four in a single whorl. Length: About 2.4 cm. Width: About 2.8 cm. Shape: Reniform, concave. Apex: Obtuse to bluntly and broadly acute. Base: Short cuneate. Margin: Entire to coarsely crenate. Texture and luster, upper and lower surfaces: Smooth, glabrous; matte. Color: When opening, upper surface: Close to 68A. When opening, lower surface: Close to 73B. Fully opened, upper surface: Close to 65A; color does not fade with development. Fully opened, lower surface: Close to between 65A and 73B; color does not fade with development.

*Pedicels, fertile flowers*.—Length: About 4 mm. Diameter: About 1 mm. Strength: Moderately strong. Aspect: Mostly upright, about 10° from vertical. Texture and luster: Smooth, glabrous; matte. Color: Close to 185C.

*Pedicels, sterile flowers*.—Length: About 2.9 cm. Diameter: About 2 mm. Strength: Moderately strong. Aspect: About 30° from vertical. Texture and luster: Sparsely pubescent; matte. Color: Close to 73A; fading proximally to close to 182B.

*Reproductive organs, fertile flowers*.—Stamens: Quantity per flower: About ten. Filament length: About 1.5 mm. Filament color: Close to NN155B. Anther length: About 1 mm. Anther shape: Broadly oblong. Anther color: Close to 155A. Pollen amount: None observed. Pistils: Pistil quantity per flower: About three or occasionally two. Pistil length: About 1.5 mm. Stigma shape: Club-shaped. Stigma color: Close to 75D to lighter than 75D. Style length: About 0.5 mm. Style color: Close to 70C. Ovary color: Close to 145C.

*Reproductive organs, sterile flowers*.—Stamens: Quantity per flower: About eight. Filament length: About 1.5 mm. Filament color: Close to NN155B. Anther length: About 1 mm. Anther shape: Broadly oblong. Anther color: Close to 155A. Pollen amount: None observed. Pistils: Pistil quantity per flower: About two. Pistil length: About 1.5 mm. Stigma shape: Club-shaped. Stigma color: Close to 75D to lighter than 75D. Style length: About 0.5 mm. Style color: Close to 70C. Ovary color: Close to 70C.

*Seeds*.—To date, seed development has not been observed on plants of the new *Hydrangea*.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 to 9.

It is claimed:

1. A new and distinct *Hydrangea* plant named 'Hokomarore' as illustrated and described.

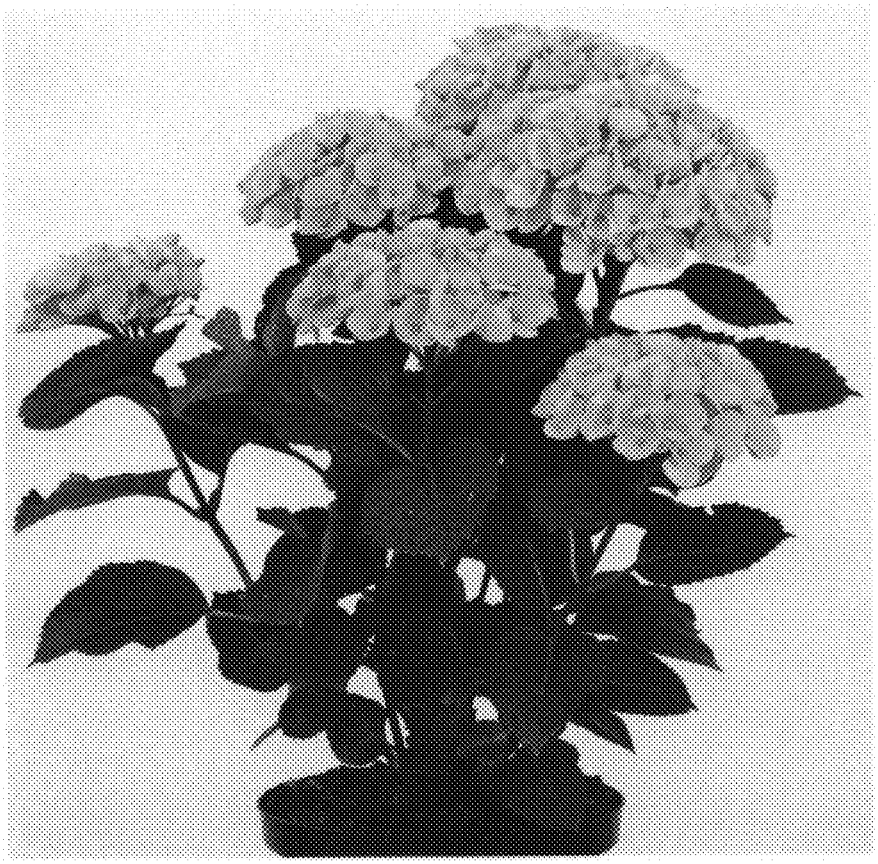

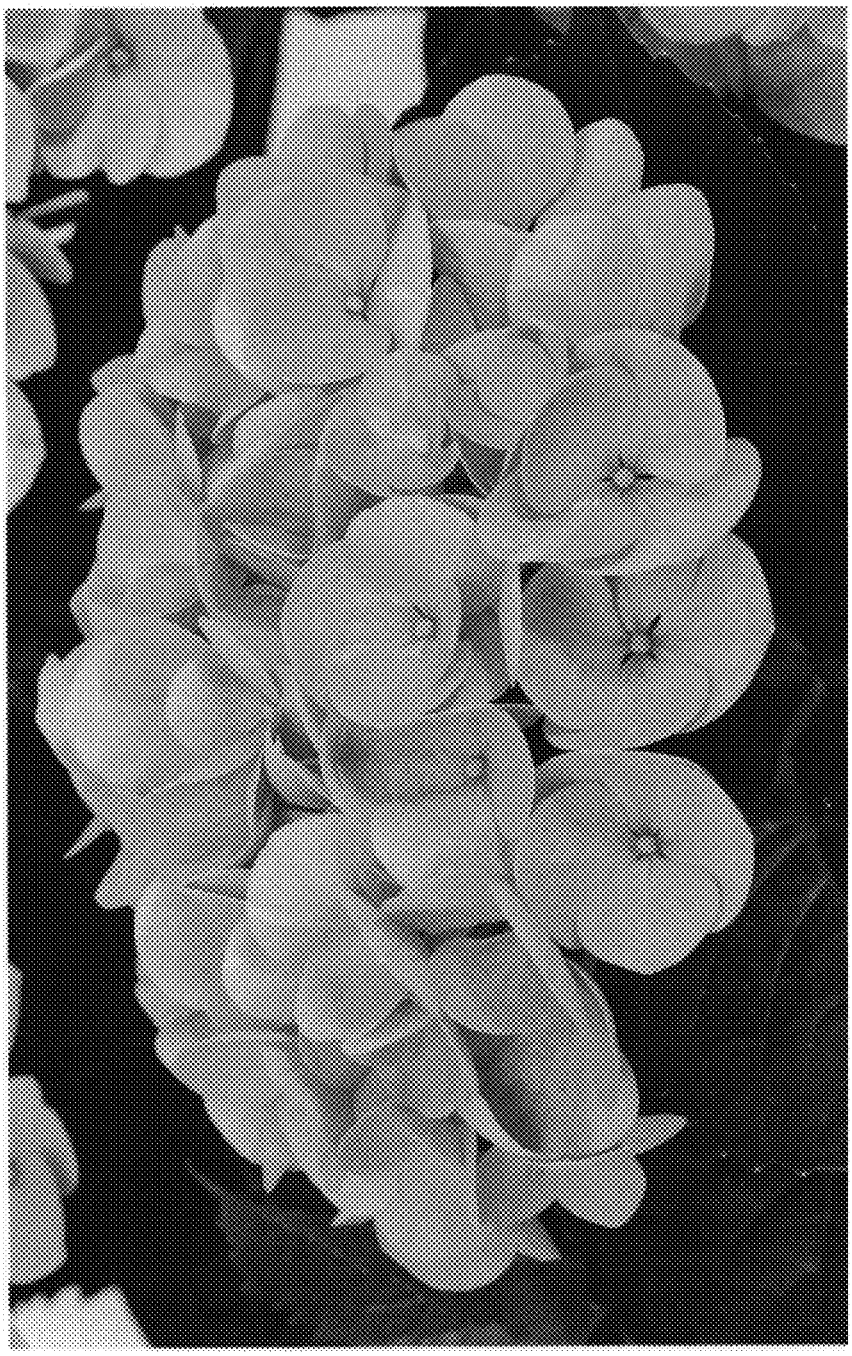

* * * * *